US011426563B2

United States Patent
Rowe et al.

(10) Patent No.: US 11,426,563 B2
(45) Date of Patent: Aug. 30, 2022

(54) BLOOD PUMP OR BALLOON CYCLING AND VENOUS OCCLUSION

(71) Applicant: NXT Biomedical, LLC, Irvine, CA (US)

(72) Inventors: Stanton J. Rowe, Irvine, CA (US); Joseph Passman, Irvine, CA (US); Glen Rabito, Irvine, CA (US); Robert C. Taft, Irvine, CA (US); Alexander Siegel, Irvine, CA (US)

(73) Assignee: NXT Biomedical, LLC, Irvine, CA (US)

( * ) Notice: Subject to any disclaimer, the term of this patent is extended or adjusted under 35 U.S.C. 154(b) by 0 days.

(21) Appl. No.: 17/297,988

(22) PCT Filed: Dec. 3, 2019

(86) PCT No.: PCT/US2019/064292
§ 371 (c)(1),
(2) Date: May 27, 2021

(87) PCT Pub. No.: WO2020/117844
PCT Pub. Date: Jun. 11, 2020

(65) Prior Publication Data
US 2022/0001154 A1 Jan. 6, 2022

Related U.S. Application Data

(60) Provisional application No. 62/849,759, filed on May 17, 2019, provisional application No. 62/774,787, filed on Dec. 3, 2018.

(51) Int. Cl.
*A61M 25/10* (2013.01)

(52) U.S. Cl.
CPC .. *A61M 25/10184* (2013.11); *A61M 25/1011* (2013.01); *A61M 2025/1052* (2013.01); *A61M 2210/1082* (2013.01)

(58) Field of Classification Search
CPC ........ A61M 25/10184; A61M 25/1011; A61M 25/1052; A61M 2025/1059
See application file for complete search history.

(56) References Cited

U.S. PATENT DOCUMENTS

| 3,504,662 A | 4/1970 | Jones |
| 3,505,987 A | 4/1970 | Heilman |
| (Continued) | | |

FOREIGN PATENT DOCUMENTS

| DE | 244694 A1 | 4/1987 |
| EP | 0209070 A2 | 1/1987 |
| (Continued) | | |

OTHER PUBLICATIONS

WIPO, U.S. International Search Authority, International Search Report and Written Opinion dated Feb. 7, 2020 in International Patent Application No. PCT/US2019/064292, 9 pages.

(Continued)

*Primary Examiner* — Nathan R Price
*Assistant Examiner* — Melissa A Snyder
(74) *Attorney, Agent, or Firm* — Inskeep IP Group, Inc.

(57) ABSTRACT

Several embodiments of a catheter are described, having a balloon configured to slowly inflate and then quickly deflate to create an area of low pressure in the vessels. The balloon can be cycled near the vessels of the kidneys, thereby helping to draw out blood from the kidneys and enhance fluid processing to the bladder.

20 Claims, 17 Drawing Sheets

(56) References Cited

U.S. PATENT DOCUMENTS

| | | | |
|---|---|---|---|
| 3,692,018 A | 9/1972 | Goetz et al. | |
| 3,939,820 A | 2/1976 | Grayzel | |
| 4,522,195 A | 6/1985 | Schiff | |
| 4,527,549 A | 7/1985 | Gabbay | |
| 4,546,759 A | 10/1985 | Solar | |
| 4,697,574 A | 10/1987 | Karcher et al. | |
| 4,902,272 A | 2/1990 | Milder et al. | |
| 5,176,619 A | 1/1993 | Segalowitz | |
| 5,820,542 A | 10/1998 | Dobak, III et al. | |
| 6,136,025 A | 10/2000 | Barbut et al. | |
| 6,228,018 B1 | 5/2001 | Downey et al. | |
| 7,172,551 B2 | 2/2007 | Leasure | |
| 7,374,531 B1 | 5/2008 | Kantrowitz | |
| 7,914,436 B1 | 3/2011 | Kung | |
| 7,927,268 B1 | 4/2011 | St. Germain et al. | |
| 8,221,303 B2 | 7/2012 | Ovil et al. | |
| 8,579,788 B2 | 11/2013 | Orejola | |
| 10,137,231 B2 | 11/2018 | Anagnostopoulos | |
| 10,245,363 B1 | 4/2019 | Rowe | |
| 2009/0099516 A1* | 4/2009 | Gildoni | A61M 60/135 604/99.01 |
| 2010/0241047 A1 | 9/2010 | Yacoubian et al. | |
| 2011/0190867 A1* | 8/2011 | Vonderwalde | A61F 2/958 623/1.11 |
| 2018/0169313 A1* | 6/2018 | Schwammenthal | A61M 60/40 |
| 2019/0083689 A1 | 3/2019 | Anagnostopoulos | |
| 2019/0167878 A1 | 6/2019 | Rowe | |

FOREIGN PATENT DOCUMENTS

| | | |
|---|---|---|
| NL | 2022661 | 9/2020 |
| SU | 1001928 A1 | 3/1983 |
| WO | WO 2000/53240 A1 | 9/2000 |
| WO | WO 2014/203078 A2 | 12/2014 |
| WO | WO 2020/053663 A1 | 3/2020 |
| WO | WO 2020/087125 A1 | 5/2020 |
| WO | WO 2020/180176 A1 | 9/2020 |

OTHER PUBLICATIONS

Daemen, J., "Ventricular counterpulsation for percutaneous ventricular support—Pulsecath," Erasmus MC University Medical Center Rotterdam, Sep. 22, 2018, 10 pages.

Bregman, D. et al., "Left ventricular and unidirectional intra-aortic balloon pumping Effects on hemodynamics in canine cardiogenic shock," *The Journal of Thoracic and Cardiovascular Surgery*, vol. 68, No. 5, Nov. 1974, pp. 677-686.

* cited by examiner

BLOOD PUMP OR BALLOON CYCLING AND VENOUS OCCLUSION

RELATED APPLICATIONS

This application is the U.S. National Phase of and claims priority to International Patent Application No. PCT/US2019/064292, International Filing Date Dec. 3, 2019, entitled Blood Pump Or Balloon Cycling And Venous Occlusion; which claims benefit of U.S. Provisional Application Ser. No. 62/774,787 filed Dec. 3, 2018 entitled Creating Low Pressure Zones Within The Cardiovascular System Via Balloon Pulsation; and U.S. Provisional Application Ser. No. 62/849,759 filed May 17, 2019 entitled Blood Pump Or Balloon Cycling And Venous Occlusion; all of which are incorporated herein by reference in their entireties.

BACKGROUND OF THE INVENTION

Acute decompensated heart failure (ADHF) generally occurs when the heart is incapable of circulating an adequate blood supply to the body. This is typically due to inadequate cardiac output, which has many causes. In ADHF decompensation, fluids back up in a retrograde direction through the heart, lungs and venous/lymphatic systems throughout the body, causing discomfort and organ dysfunction. One hallmark of recurrent hospitalization due to ADHF is resistance to increasing diuretic dosages. This leads to longer hospital stays and/or ineffective decongestion.

In addition to fatigue, one of the prominent features of congestive heart failure is the retention of fluids within the body. Commonly, gravity causes the retained fluid to accumulate to the lower body, including the abdominal cavity, liver, kidneys, interstitial spaces, lymphatics, abdominal cavity, resulting in numerous related complications. Fluid restriction and a decrease in salt intake can be helpful to manage the fluid retention, but diuretic medications are the principal therapeutic option, including furosemide, bumetanide, and hydrochlorothiazide. Additionally, vasodilators and inotropes may also be used for treatment.

While diuretics can be helpful, they are also frequently toxic to the kidneys and if not used carefully, can result in acute and/or chronic renal failure. This mandates careful medical management while in a hospital, consuming large amounts of time and resources. Hence, the ability to treat fluid retention from congestive heart failure without the need for toxic doses of diuretics would likely result in better patient outcomes at substantially less cost.

Fluid retention is not limited only to ADHF. Other conditions such as organ failure, cirrhosis, hepatitis, cancer, and infections can also cause fluid buildup in various areas of the body. However, these conditions can often benefit from similar fluid treatment techniques.

In this regard, what is needed is an improved treatment option for fluid buildup in the body, whether that buildup is caused by ADHF, cirrhosis, organ failure, cancer, infections, or other underlying diseases.

OBJECTS AND SUMMARY OF THE INVENTION

In some embodiments, the present invention discloses a renal perfusion enhancement device for enhancing renal performance by lowering inferior vena cava pressure, comprising a balloon on a catheter and a guidewire. The catheter is inserted through femoral artery and guided in the inferior vena cava over the guidewire and the balloon is placed either inside or next to the renal veins. The balloon is slowly inflated first and then rapidly deflated to create a low-pressure zone in a vessel. The end result is an improved filtration gradient, which increases glomerular filtration and ultimately urine output. Glomerular filtration is the first step in making urine and it is the process that kidneys use to filter excess fluid and waste products out of the blood into the urine collecting tubules of the kidneys, so they may be eliminated from the body.

In other embodiments, the present invention discloses renal perfusion enhancement devices comprising an upstream balloon and a downstream balloon, placed either on the same catheter or on different catheters. The downstream balloon is slowly inflated and rapidly deflated to create a low-pressure zone to which results an improved filtration gradient that increases glomerular filtration and ultimately urine output.

In some other embodiments, the present invention discloses renal perfusion enhancement devices comprising an upstream balloon and a downstream pump, placed either on the same catheter or on different catheters. The downstream pump activation creates a low-pressure zone resulting in an improved filtration gradient that increase urine output from the kidneys and fluid removal from the body.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
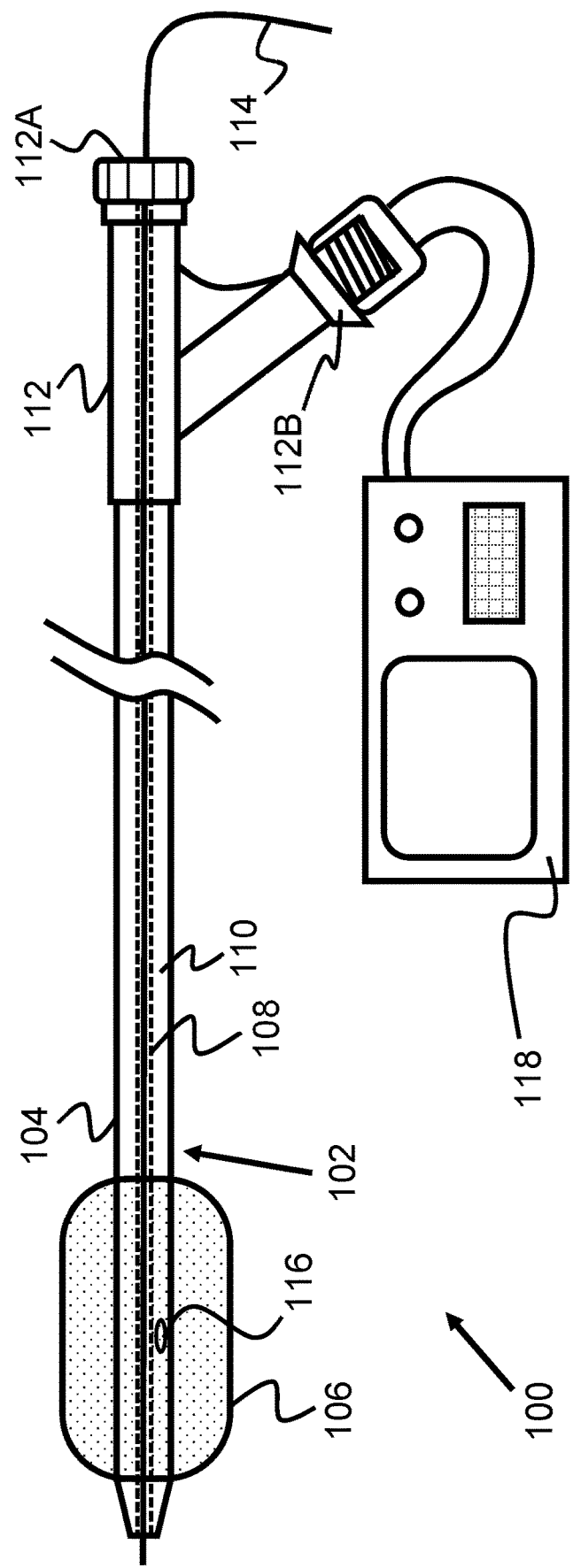
FIG. 1 illustrates one embodiment of a renal perfusion enhancement system through balloon pulsation using a balloon, a catheter, and a guide wire.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. In that respect, elements and functionality of one embodiment not necessarily only limited to that embodiment and may be combined with other embodiments shown herein in any manner that would result in a functional embodiment. The terminology used in the detailed description of the embodiments illustrated in the accompanying drawings is not intended to be limiting of the invention. In the drawings, like numbers refer to like elements, including between different embodiments. While different embodiments are disclosed in this specification, it should be understood that the features of each embodiment can be combined with features of other embodiments. In other words, each embodiment is not intended to necessarily be the final version of an embodiment, but rather different features of each embodiment can be mixed, matched, and combined.

It is common for cardiac dysfunction, such as, acute decompensated heart failure (ADHF) to develop kidney dysfunction symptoms. Typically, ADHF causes systemic venous congestion, which gives rise to an increase in renal venous and interstitial pressure. The increase in the venous pressure causes fluid retention, driven by resultant inefficiencies in the kidneys, to increase. The resulting fluid retention develops or worsen acute decompensated heart failure by causing a blood volume overload in the heart.

The present invention is generally directed to devices and methods for treating excessive fluid retention driven by the kidneys which may result from conditions such as acute decompensated heart failure. Generally, the present invention offloads fluid volume of the kidneys by increasing blood flow through the kidneys and potentially offloading interstitial pressure.

In some embodiments, the present invention discloses a renal perfusion enhancement device comprising a balloon on a catheter and a guidewire. The catheter is inserted through femoral vein and guided in the inferior vena cava over the guidewire and the balloon is placed either inside or next to the renal veins. The balloon is slowly inflated first and then rapidly deflated to create a low-pressure zone in a vessel resulting in fluid being pulled out of the kidneys. The creation of low pressure in the renal veins increases the pressure gradient between the renal arteries and renal veins. This mechanism drives increased renal blood flow and increases filtration and ultimately increases urine output.

In other embodiments, the present invention discloses renal perfusion enhancement devices comprising an upstream balloon and a downstream balloon, placed either on the same catheter or on different catheters. The downstream balloon is slowly inflated and rapidly deflated to create a low-pressure zone to pull fluid out of the kidneys. In some other embodiments, the present invention discloses renal perfusion enhancement devices comprising an upstream balloon and a downstream pump, placed either on the same catheter or on different catheters. The downstream pump activation creates a low-pressure zone resulting fluid to pull out of the kidneys. Use of these devices to treat excessive fluid retention through improved renal function may significantly reduce the duration of hospital stay for patients in comparison to the treatment of the same condition through diuretics.

FIG. 1 illustrates one embodiment of a renal perfusion enhancement device 100 that may be used to drain the excessive fluid retention through improved renal function of the kidneys of a patient. The device 100 comprises a catheter 102 having an inflation lumen 110 located within an outside wall 104 of the catheter 102, and a central lumen 108 disposed within the inflation lumen 110 creating a passageway for a guidewire 114. The guidewire 114 is inserted in the central lumen 108 of the catheter 102 through an opening 112A (e.g., a Touhy-Borst connector) connected to the catheter hub 112 at the proximal end of the catheter 102. A balloon 106 is positioned at the distal portion of the catheter 102.

Inflation and deflation of the balloon 106 is accomplished through an inflation aperture 116 connected to the inflation lumen 110 inside the balloon 106. The inflation lumen 110 of the catheter 102 is connected to a pump (liquid or, preferably, pneumatic) system 118 through a connector hub opening 112B. The pump system 118 controls the operation of a pump through a central processing unit (not shown in the figure) to inflate and deflate the balloon 106 positioned at the distal portion of the catheter 102.

In all the embodiments of renal perfusion enhancement device disclosed in the FIGS. 1-21, the catheter 102 with the attached balloon 106 (in a deflated state) can be inserted into the body of a patient through the femoral vein (not shown in figures) and into the inferior vena cava 12 over the guidewire 114. The balloon 106 may then be placed either inside or next to the right renal vein 14A or left renal vein 14B stemming out of the right kidney 10A and left kidney 10B, as may be best seen in FIGS. 2-5.

Figure 2:
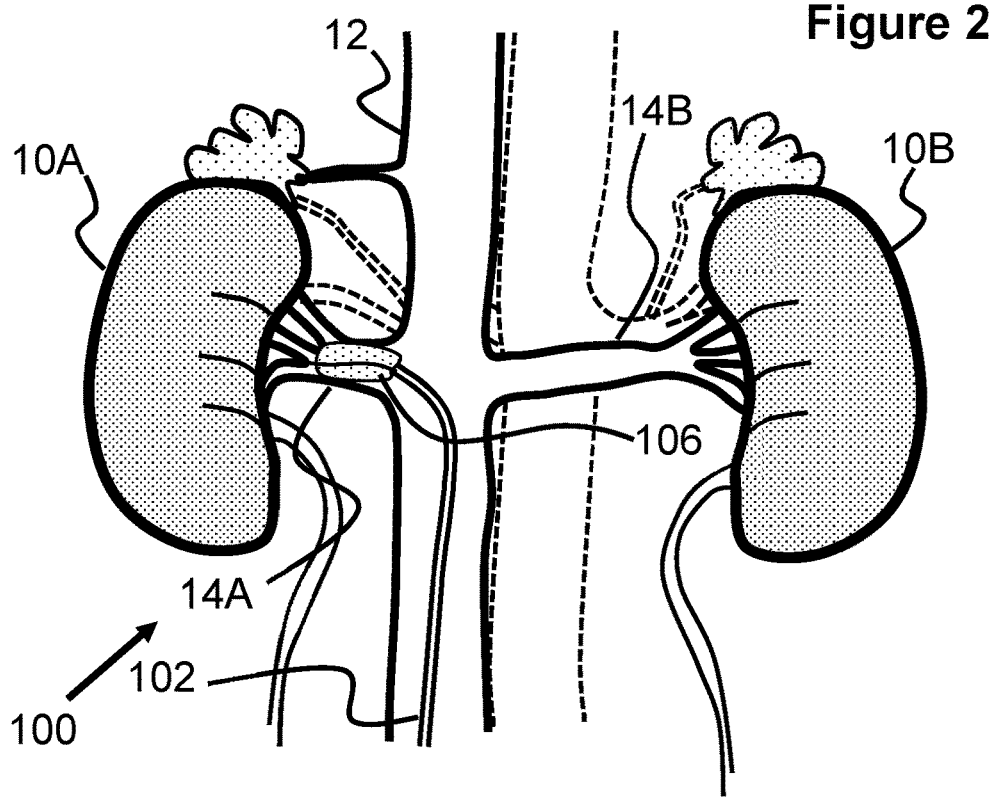
FIG. 2 illustrates the balloon of the renal perfusion enhancement system in an inflated state inside the right renal vein.

As seen in FIG. 2, once the distal end of the catheter 102 with the deflated balloon is positioned at the desired location inside the right renal vein 14A, the balloon 106 is slowly and gradually inflated through the controlled operation of the pump system 118 through the inflation aperture 116 of the balloon 106. The inflation media may be either liquid or gas. Once inflated to a desired level, the balloon 106 is rapidly deflated to create a low-pressure zone inside the right renal vein 14A. This rapid change of pressure inside the right renal vein 14A causes more fluid to be pulled out of the right kidney 10A, as can be seen best in FIG. 3. The same process can be repeated by placing the balloon 106 in the left renal vein 14B. Notably, the slow and gradual inflation of the balloon 106 does not cause a rapid increase in pressure in the renal veins, and, therefore, does not impact the pressure gradient between the renal artery and renal venous system.

Figure 3:
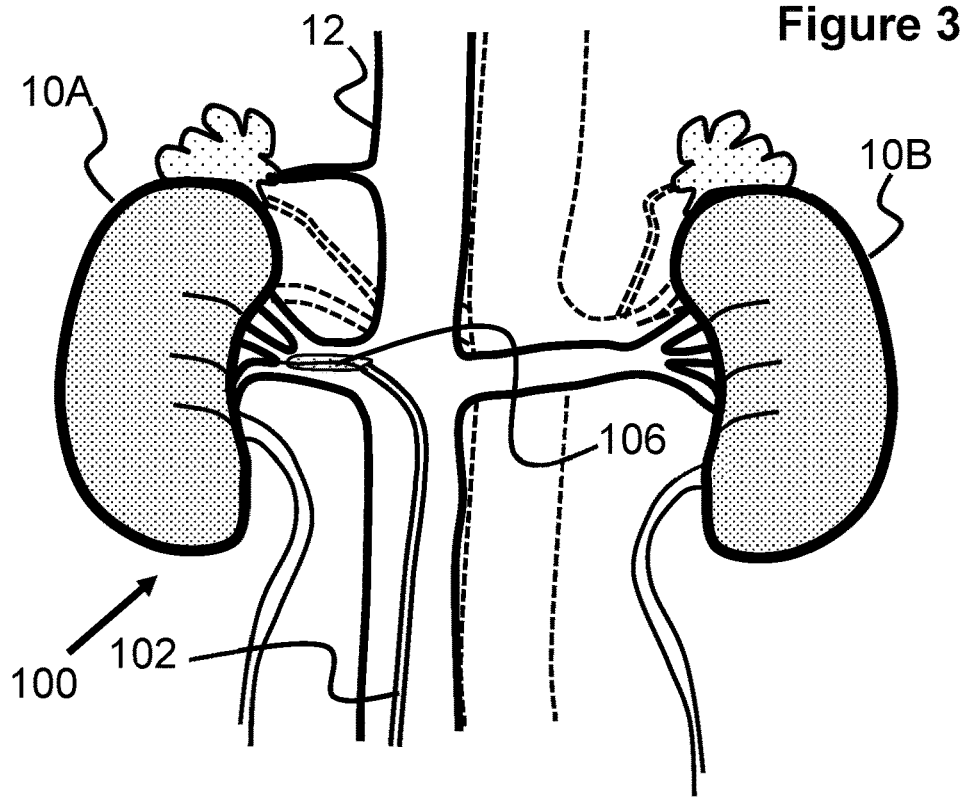
FIG. 3 illustrates the balloon of the renal perfusion enhancement system in a deflated state inside right renal vein.
Figure 4:
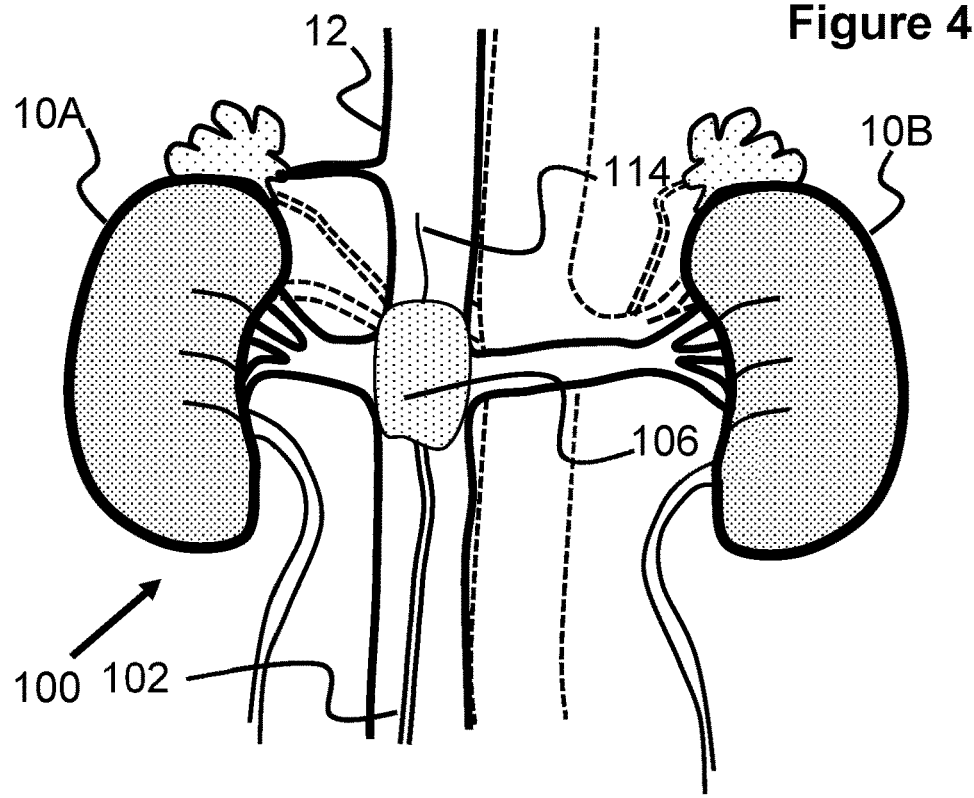
FIG. 4 illustrates a balloon of the renal perfusion enhancement system in an inflated state inside the inferior vena cava.
Figure 5:
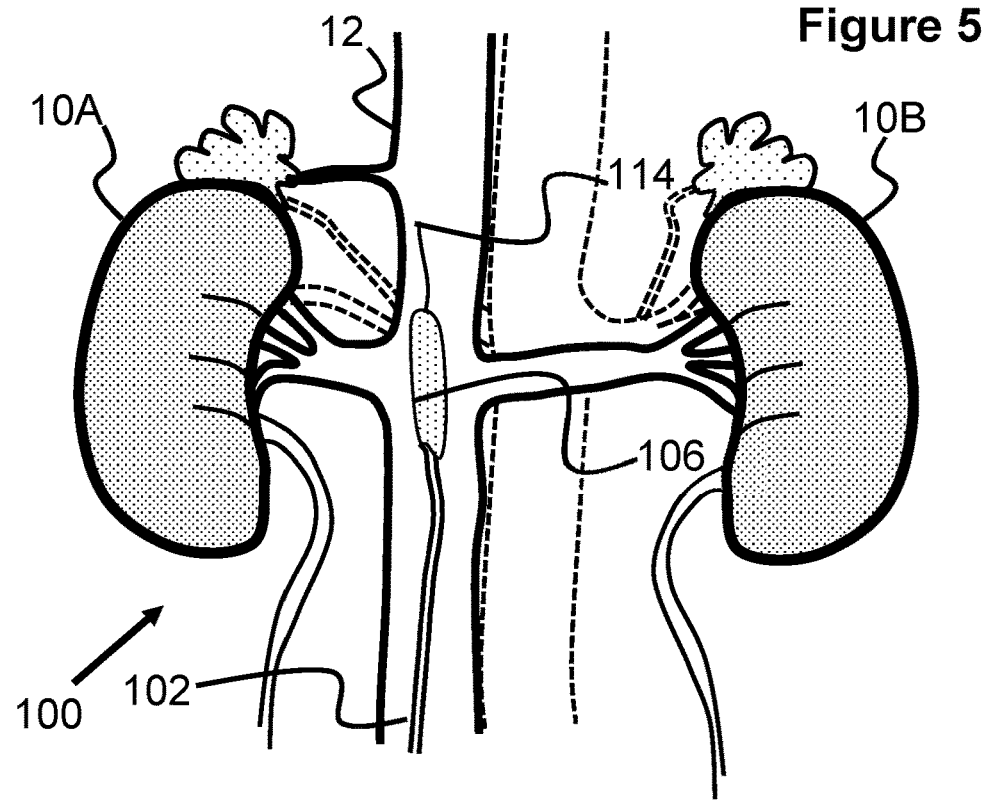
FIG. 5 illustrates the balloon of the renal perfusion enhancement system in a deflated state inside the inferior vena cava.

In addition to placing the balloon 106 inside the renal veins 14A or 14B as illustrated in FIGS. 2-3, FIG. 4 demonstrates that the balloon 106 may also be placed inside the inferior vena cava 12 and next to the right renal vein 14A and left renal vein 14B. Once the balloon 106 is placed at the desired location, the pump system 118 slowly and gradually inflates the balloon 106 through the inflation aperture 116. Once inflated to a desired level, the balloon 106 is rapidly deflated to create a low-pressure zone in a high-pressure gradient inside the vena cava 12. This rapid change of pressure inside the inferior vena cava 12 creates a low-pressure zone in a high-pressure gradient. This rapid change of pressure causes fluid to be pulled across the right kidney 10A and the left kidney 10B, as can be seen best in FIG. 5.

Figure 6:
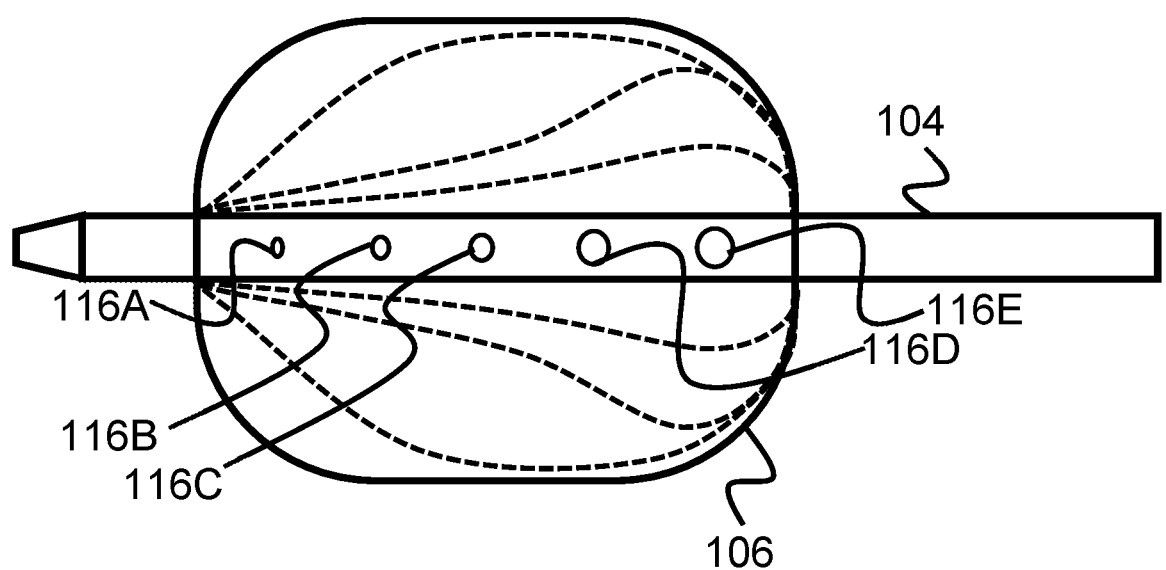
FIG. 6 illustrates progressive inflation of a balloon of the renal perfusion enhancement system through various sizes of inflation apertures.

While the balloon 106 can uniformly inflate and deflate in diameter to create the low-pressure zones in the vessels, the balloon 106 can also be constructed to inflate in a manner that progressively increases in diameter along the length of the balloon 106 as inflation pressure increases. FIG. 6 illustrates this progressive inflation of the balloon 106 and the dotted lines indicate profiles of the balloon 106 at various stages of inflation. The progressive inflation can be achieved, for example, either by using various diameters of the inflation apertures 116A-116E, by using a balloon 106 with areas of different elasticity or hardness along the length, or both. In FIG. 6, the smallest diameter inflation aperture 116A provides slowest inflation of that portion of the balloon 106 and the largest diameter inflation aperture 116E provides fastest inflation of that portion of the balloon 106. Similarly, the balloon 106 may be constructed comprising different sections with different resistance of expansion, which allows sections with the least resistance to expansion to expand first and sections with greater resistance to expansion to expand later. For example, areas of the balloon 106 with the least elasticity (e.g. non-elastic) tend to inflate first while areas with greater elasticity tend to require greater inflation pressures to expand. The pump system 118 automatically controls the progressive inflation of the balloon 106 through these varying diameters of the inflation apertures 116A-116E. The progressive inflation profile of the balloon 106 tends to push the blood in a forward direction as it gradually inflates through apertures 116A-116E or through areas of different elasticity or hardness along the length of the balloon 106. Hence, not only is blood moved by creating a low-pressure region in the vessels during deflation of the balloon 106, it also moves blood during inflation too.

Figure 7:
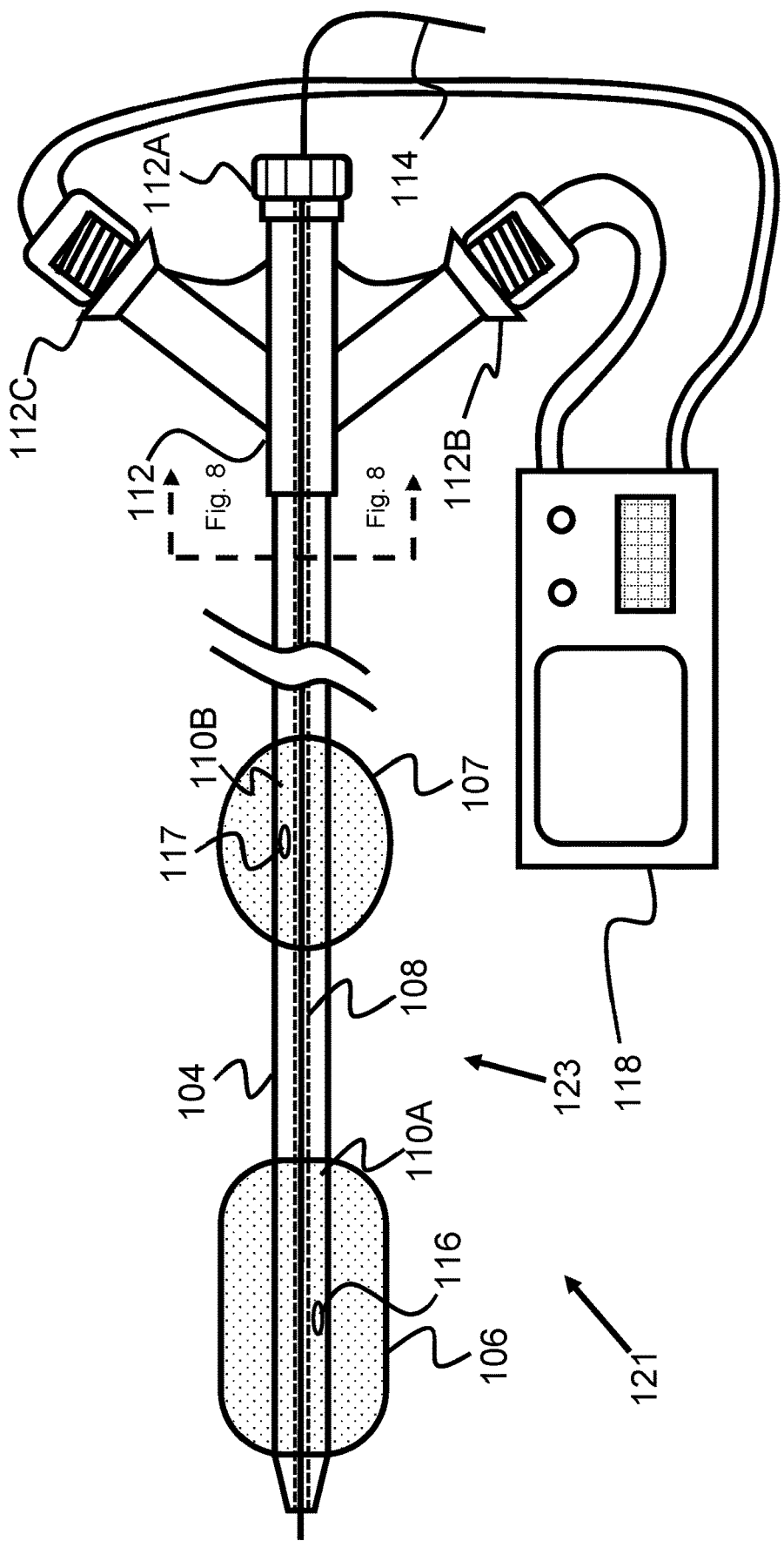
FIG. 7 illustrates a second embodiment of the renal perfusion enhancement system using an upstream balloon, a downstream balloon, a catheter and a guide wire.

FIG. 7 describes a second embodiment of the renal perfusion enhancement device 121 which comprises a single catheter 123 having an inflation lumen 110 placed within an outside wall 104 of the catheter 123, and a central lumen 108 disposed within the inflation lumen 110 creating a passageway for a guidewire 114. The guidewire 114 is inserted in the central lumen 108 of the catheter 123 through an opening 112A (e.g., a Touhy-Borst connector) connected to the catheter hub 112 at the proximal end of the catheter 123. A first downstream cycling balloon 106 is positioned at the distal portion of the catheter 123 and a second upstream occlusive balloon 107 is positioned at a proximal direction away from the downstream cycling balloon 106 of the catheter 123. Inflation and deflation of the downstream cycling balloon 106 is accomplished through one or more inflation apertures 116 placed in the inflation lumen 110A inside the downstream cycling balloon 106 and the inflation and deflation of the upstream occlusive balloon 107 is accomplished through inflation aperture 117 connected to the inflation lumen 110B inside the upstream occlusive balloon 107. The inflation lumens 110A of the catheter 123 are connected to a pump system 118 through a connector hub opening 112B and the inflation lumen 110B of the catheter 123 is connected to the pump system 118 through a connector hub opening 112C. The pump system 118 controls the operation of a pump to inflate and deflate the downstream cycling balloon 106 and the upstream occlusive balloon 107 of the catheter 123.

Figure 8:
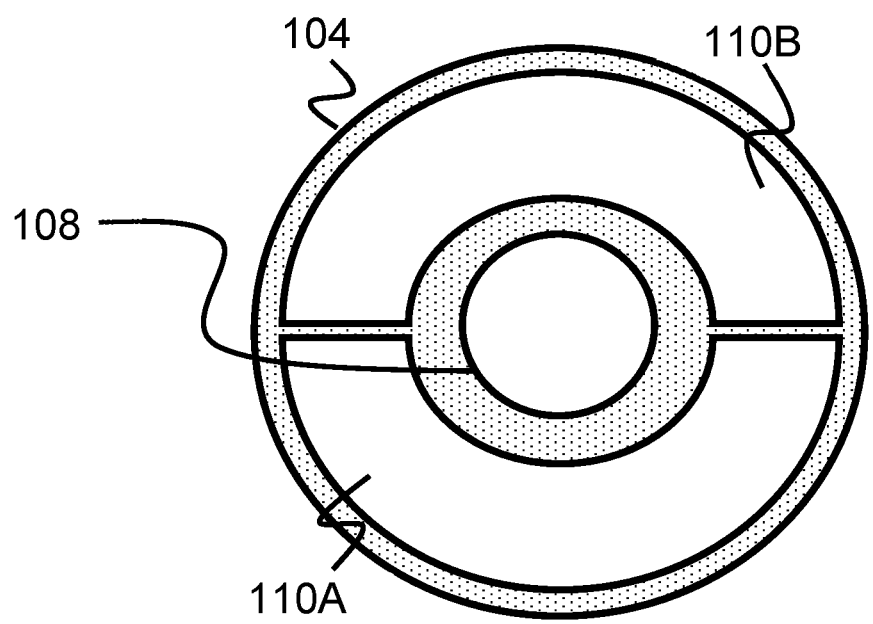
FIG. 8 illustrates the cross-section of the catheter lumen and guidewire of FIG. 7.

The cross-section of the inflation lumens 110A and 110B and the guidewire 114 of the second embodiment shown in FIG. 8. The central circle 114 represents the guidewire lumen 114, the portion labelled by 110A is the inflation lumen of the downstream cycling balloon 106, and the portion labelled by 110B is the inflation lumen of the upstream occlusive balloon 107. It should be understood that this configuration is merely an example and other lumen configurations are also possible.

Figure 9:
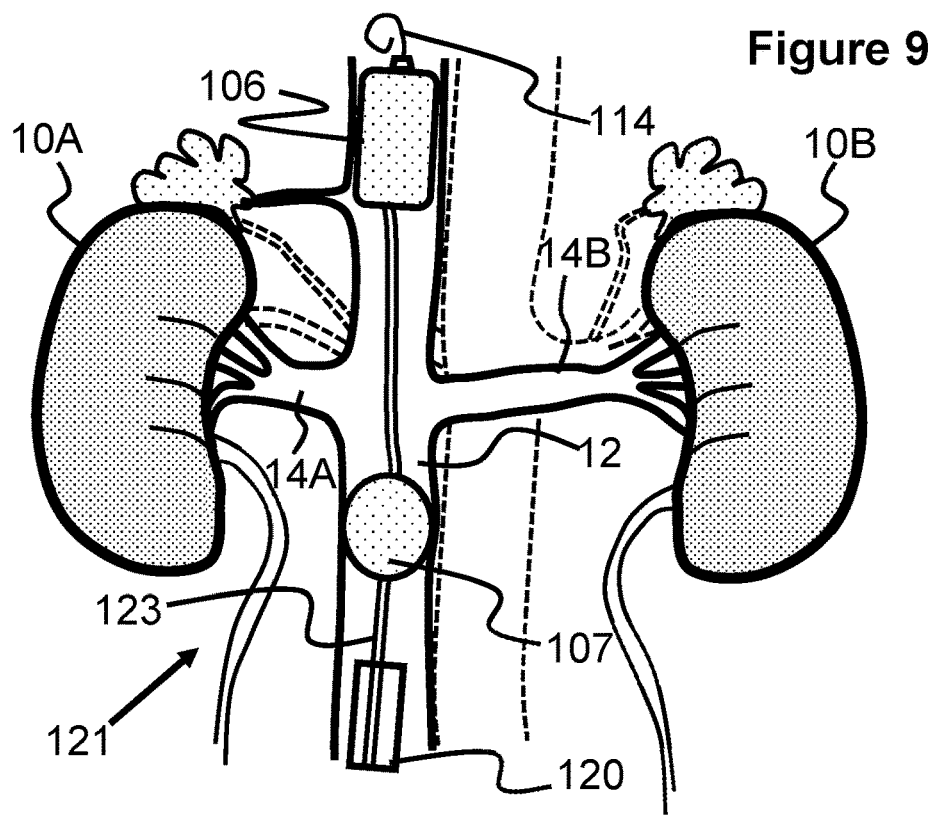
FIG. 9 illustrates the upstream balloon and the downstream balloon of the second embodiment in inflated states inside the inferior vena cava.
Figure 10:
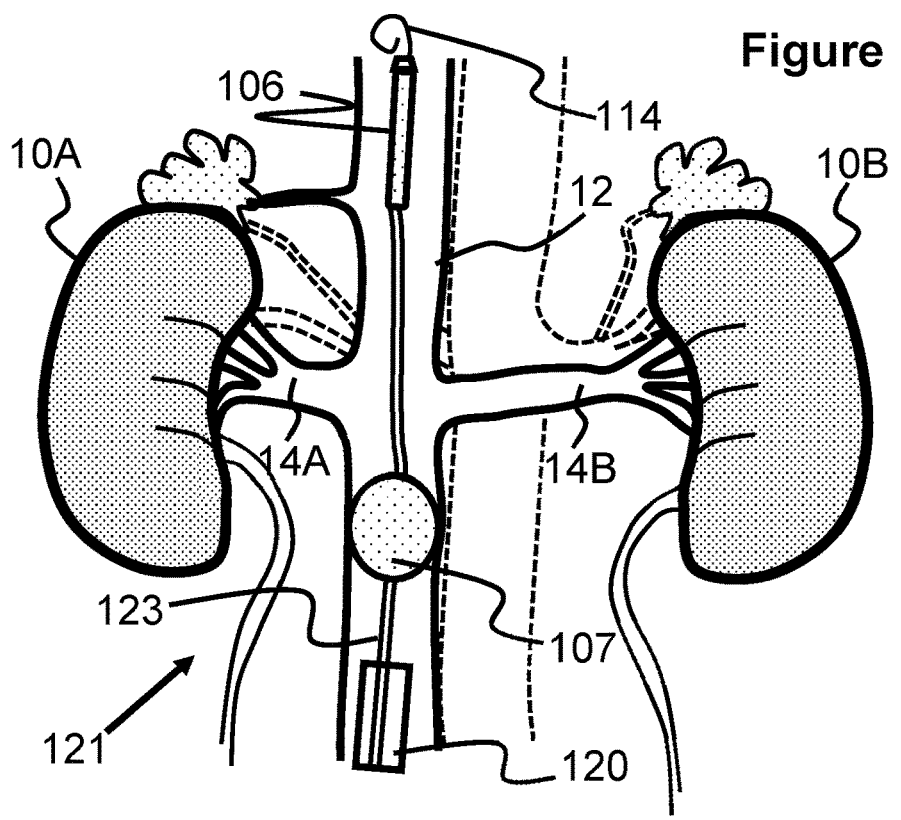
FIG. 10 illustrates the downstream balloon of the second embodiment in a deflated state and the upstream balloon of the second embodiment in an inflated state inside the inferior vena cava.

As illustrated in FIG. 9, a guidewire 114 is used to make the initial entry into the inferior vena cava 12 of a patient, the access sheath 120 is inserted into the vena cava 12, and the catheter 123 is advanced over the guidewire 114. Once the catheter 123 is positioned at the desired location inside the inferior vena cava 12 and next to the right renal vein 14A and left renal vein 14B, the upstream occlusive balloon 107 is inflated first by the controlled operation of the pump system 118 through the inflation aperture 117. Next, the downstream cycling balloon 106 is slowly inflated through the inflation aperture 116 of the cycling balloon 106. Once the downstream cycling balloon 106 is inflated to a desired level, the downstream cycling balloon 106 is rapidly deflated. This rapid deflation of the downstream cycling balloon 106 creates a low-pressure zone, which results in fluid in the renal system to be pulled across the right kidney 10A and the left kidney 10B, as can be seen best in FIG. 10. This inflation and deflation can be performed several times or for several minutes (e.g., 5 or more minutes) before the occlusive balloon 107 is deflated to allow normal blood flow through the vessels. Typically, the downstream cycling balloon 106 is placed within the vena cava 12 downstream of the junctions of the vena cava 12 with the patient's renal veins 14A and 14B, and the downstream cycling balloon 106 pumps blood through the vena cava 12 in the downstream direction, away from the junctions.

In the final step of this fluid drainage process, the upstream occlusive balloon 107 is deflated and the whole process is repeated over the course of several minutes to hours (e.g., up to 72 hours) to drain excess fluid from kidneys 10A and 10B. In one embodiment the process is repeated, for example, three times. Notably, the progressive and slow inflation of the downstream cycling balloon 106 does not cause a rapid increase in pressure inside the downstream portion of the vena cava 12, and, therefore, does not impact the pressure gradient between the renal artery and renal venous system.

Figure 11:
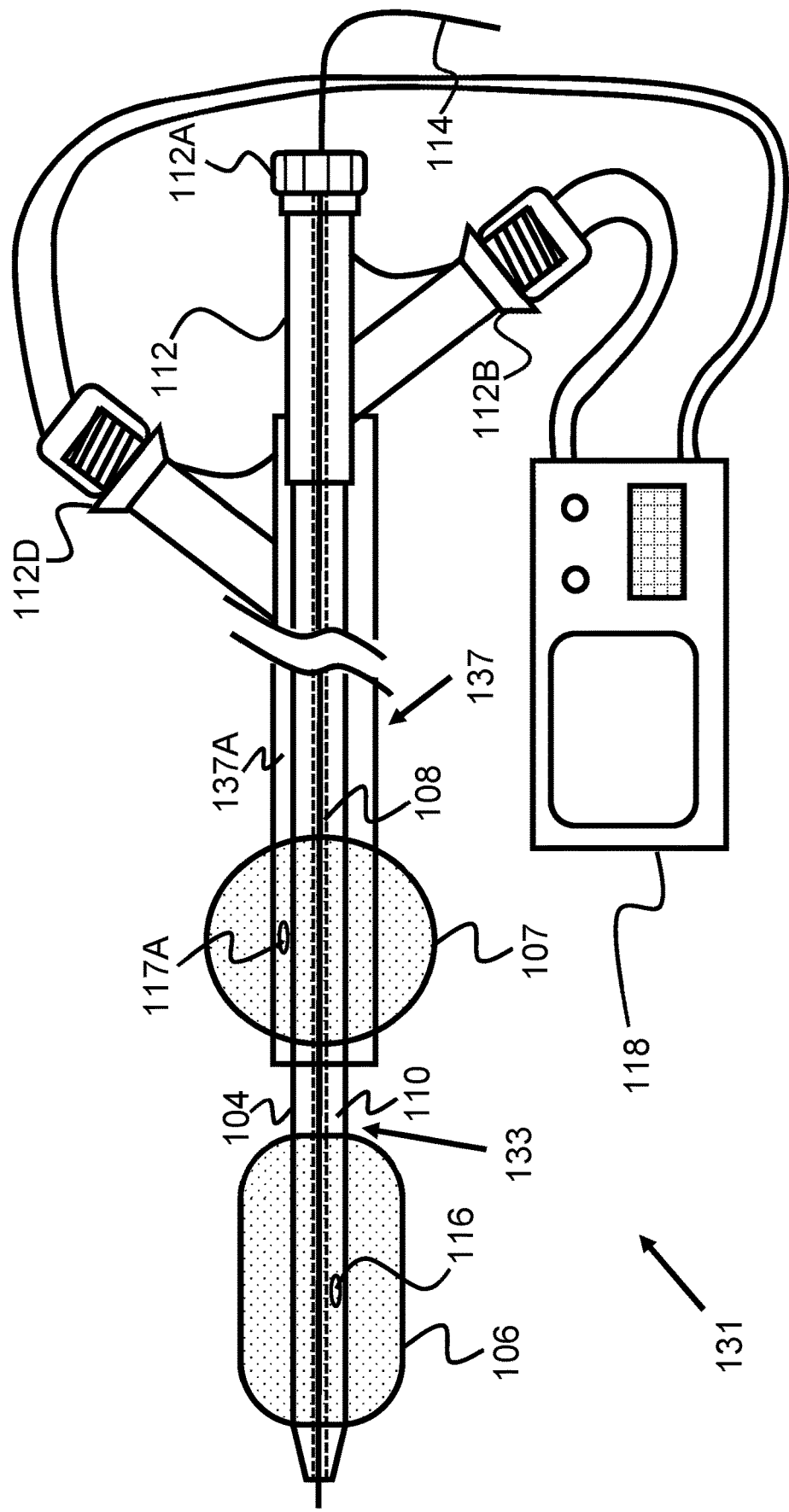
FIG. 11 illustrates a third embodiment of the renal perfusion enhancement system using the upstream balloon and the downstream balloon, two catheters and a guide wire, where the balloons are placed on different catheters.

FIG. 11 describes a third embodiment of the renal perfusion enhancement device 131 which comprises a first catheter 133 having an inflation lumen 110 located within an outside wall 104 of the catheter 133, and a central lumen 108 disposed within the inflation lumen 110 creating a passageway for a guidewire 114. The guidewire 114 is inserted in the central lumen 108 of the catheter 133 through an opening 112A (a Touhy-Borst connector) connected to the catheter hub 112 at the proximal end of the catheter 133. A downstream cycling balloon 106 is positioned at the distal portion of the catheter 133. The device 131 further comprises a second catheter 137 having an inflation lumen 137A and an inflation aperture 117A placed within the inflation lumen 137A of the catheter 137. An upstream occlusive balloon 107 is positioned at a distal end of the catheter 137. Inflation and deflation of the downstream cycling balloon 106 is accomplished through the inflation aperture 116 connected to the inflation lumen 110 inside the cycling balloon 106 and the inflation and deflation of the upstream occlusive balloon 107 is accomplished through the inflation aperture 137A connected to the inflation lumen 110C inside the occlusive balloon 107. The inflation lumen 110 and 137A are connected to a pump system 118 through a connector hub opening 112B and the inflation lumen 137A of the catheter 137 is connected to the pump system 118 through a connector hub opening 112D. The pump system 118 controls the operation of a pump to inflate and deflate the downstream cycling balloon 106 positioned at the distal end of the catheter 133 and the upstream occlusive balloon 107 positioned at the distal end of the catheter 137.

Figure 12:
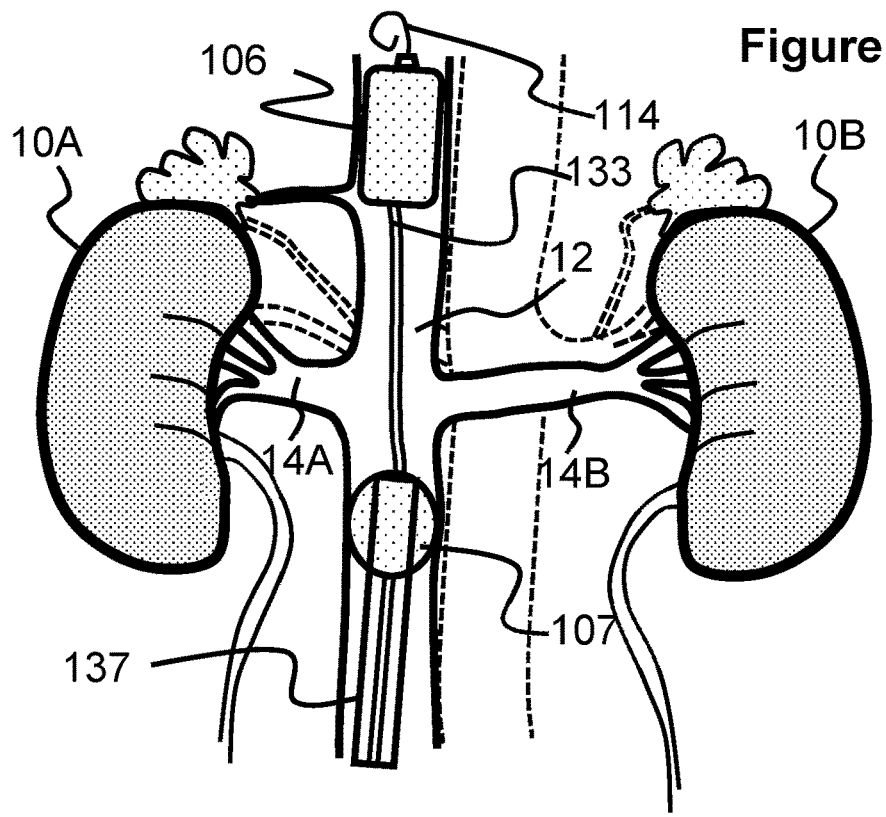
FIG. 12 illustrates the upstream balloon and the downstream balloon of the third embodiment in inflated states inside the inferior vena cava.
Figure 13:
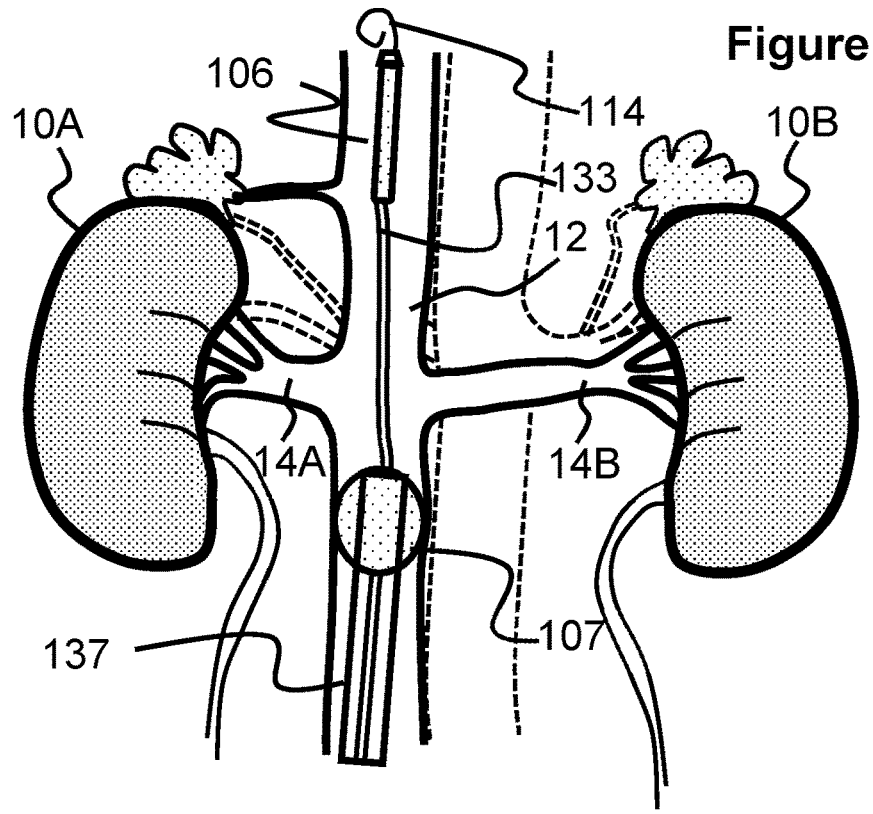
FIG. 13 illustrates the downstream balloon of the third embodiment in deflated state and the upstream balloon of the third embodiment in inflated state inside the inferior vena cava.

FIG. 12 illustrates that once the catheter 133 with the deflated downstream balloon 106 and the catheter 137 with the deflated upstream occlusive balloon 107 are positioned at the desired location inside the inferior vena cava 12, the upstream occlusive balloon 107 is inflated first by the controlled operation of the pump system 118 through the inflation aperture 117A. Next, the downstream cycling balloon 106 is slowly and progressively inflated through the inflation aperture 116 of the downstream cycling balloon 106. Once the downstream cycling balloon 106 is inflated to a desired level, the downstream cycling balloon 106 is rapidly deflated. This rapid deflation of the downstream cycling balloon 106 creates a low-pressure zone in the vessel, which results in fluid in the renal system to be pulled across the right kidney 10A and the left kidney 10B, as can be seen best in FIG. 13. This inflation and deflation cycle can be repeated several times before the occlusive balloon 107 is deflated. Typically, the downstream cycling balloon 106 is placed within the vena cava 12 downstream of the junctions of the vena cava 12 with the patient's renal veins 14A and 14B, and the downstream cycling balloon 106 pumps blood through the vena cava 12 in the downstream direction, away from the junctions.

In the final step of the renal perfusion enhancement process, the upstream occlusive balloon 107 is deflated and the whole process is repeated multiple times to drain excess fluid from kidneys 10A and 10B (e.g., enough times to achieve a target urine output of 1 or more L/day). In one embodiment, the process is repeated, for example, three time. Notably, the progressive and slow inflation of the downstream cycling balloon 106 does not cause a rapid increase in pressure inside the vena cava 12, and, therefore, does not impact the pressure gradient between the renal and venous system.

Figure 14:
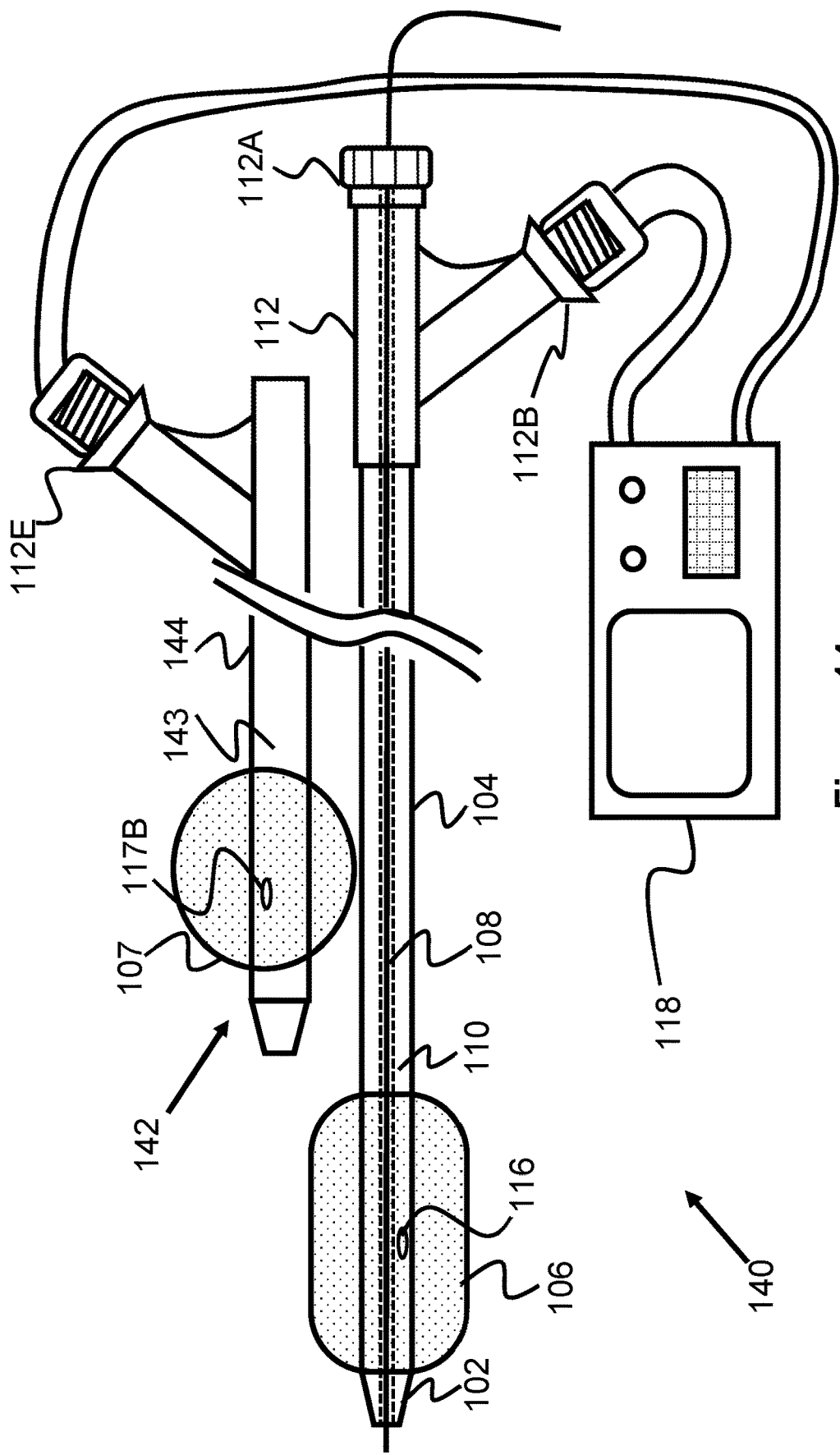
FIG. 14 illustrates a fourth embodiment of the renal perfusion enhancement system using an upstream balloon on a separate catheter and delivered through a one access sheath and a downstream balloon on another catheter.

FIG. 14 illustrates a fourth embodiment of the renal perfusion enhancement device 140 which comprises a first catheter 102 having an inflation lumen 110 placed within an outside wall 104 of the catheter 102, and a central lumen 108 disposed within the inflation lumen 110 creating a passageway for a guidewire 114. The guidewire 114 is inserted in the central lumen 108 of the catheter 102 through an opening 112A (e.g., a Touhy-Borst connector) connected to the catheter hub 112 at the proximal end of the catheter 102. A downstream cycling balloon 106 is positioned at the distal portion of the catheter 102. The device 140 further comprises a second catheter 142 having an outer catheter wall 144 forming an inflation lumen 143 and an inflation aperture 117B connected to the inflation lumen 143 of the catheter 142. The catheter 142 can be delivered through an access sheath (not shown in the drawings) into the vena cava 12 of the patient. An upstream occlusive balloon 107 is positioned at a distal end of the catheter 142. Inflation and deflation of the downstream cycling balloon 106 is accomplished through the inflation apertures 116 placed in the inflation lumen 110 inside the cycling balloon 106 and the inflation and deflation of the upstream occlusive balloon 107 is accomplished through the inflation aperture 117B placed in the inflation lumen 143 inside the occlusive balloon 107. The inflation lumen 110 of the catheter 102 is connected to a pump system 118 through a connector hub opening 112B and the inflation lumen 143 of the catheter 142 is connected to the pump system 118 through a connector hub opening 112E. The pump system 118 controls the operation of a pump to inflate and deflate the downstream cycling balloon 106 of the catheter 102 and the upstream occlusive balloon 107 of the catheter 142.

Figure 15:
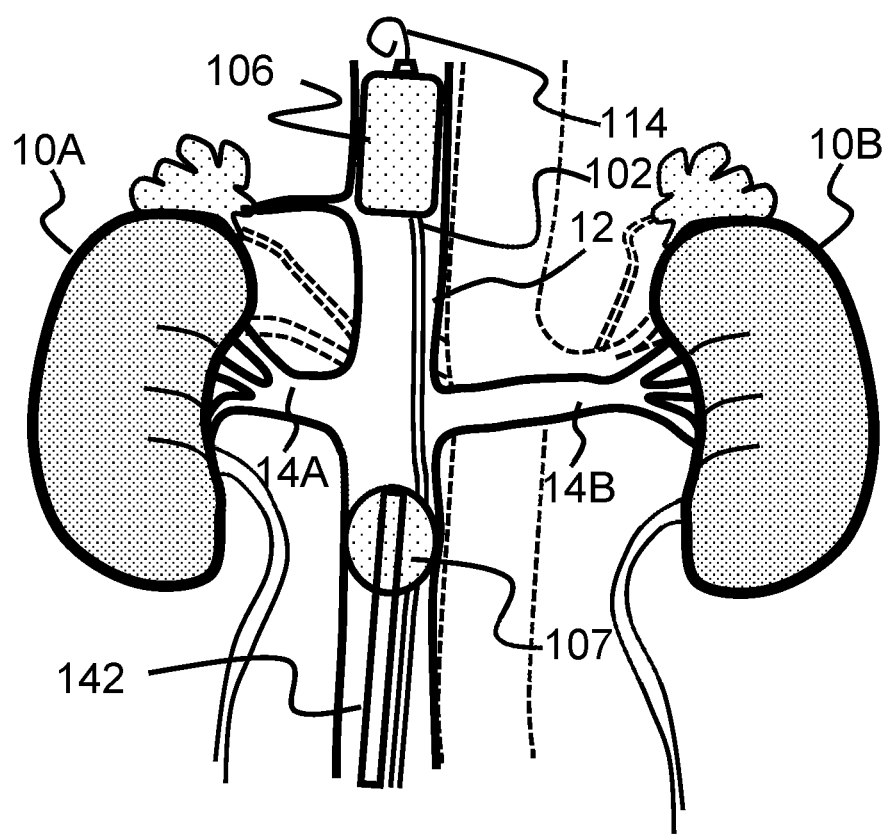
FIG. 15 illustrates the upstream and downstream balloons of the fourth embodiment in inflated states inside the inferior vena cava.

FIG. 15 illustrates that once the catheter 102 with the deflated downstream balloon 106 and the catheter 142 with the deflated upstream occlusive balloon 107 are positioned at the desired location inside the inferior vena cava 12, the upstream occlusive balloon 107 is inflated first by the controlled operation of the pump system 118 through the inflation aperture 117B. Next, the downstream cycling balloon 106 is slowly and progressively inflated through the inflation aperture 116 of the downstream cycling balloon 106. Once the downstream cycling balloon 106 is inflated to a desired level, the downstream cycling balloon 106 is rapidly deflated. This rapid deflation (which is similar to the previous embodiments and not shown in drawings) of the downstream cycling balloon 106 creates a low-pressure zone, which results in fluid in the renal system to be pulled across the kidneys. This inflation and deflation cycle can be performed multiple times before the occlusive balloon 107 is deflated. Typically, the downstream cycling balloon 106 is placed within the vena cava 12 downstream of the junctions of the vena cava 12 with the patient's renal veins 14A and 14B, and the downstream cycling balloon 106 pumps blood through the vena cava 12 the downstream direction, away from the junctions.

In the final step, the upstream occlusive balloon 107 is deflated and the whole process can be repeated several times to drain excess fluid from kidneys 10A and 10B. Notably, the progressive and slow inflation of the downstream cycling balloon 106 likely does not cause a rapid increase in pressure inside the vena cava 12, and, therefore, does not impact the pressure gradient between the renal and venous system.

The pump system 118 that is described in the context of the embodiments of this specification is configured to inflate and deflate the downstream cycling balloon 106 within certain time parameters. For example, the pump system 118 may be configured to inflate the downstream cycling balloon 106 over a relatively long period of time so as to minimize any pressure disturbances (e.g., inflation 10, 15, or 20 seconds). In another example, the pump system 118 may be configured to deflate the downstream cycling balloon 106 relatively quickly so as to cause a low-pressure region within a vessel (e.g., deflation over 1, 2, 3, or 4 seconds). These inflation and deflation patterns and times may be preprogrammed into the software of the system 118. In some embodiments, a pressure sensor on the balloon catheter 102 can be configured with the pump system 118 and the deflation and inflation times may be adjusted to hit a certain pressure or change in pressure through the sensor.

Figure 16:
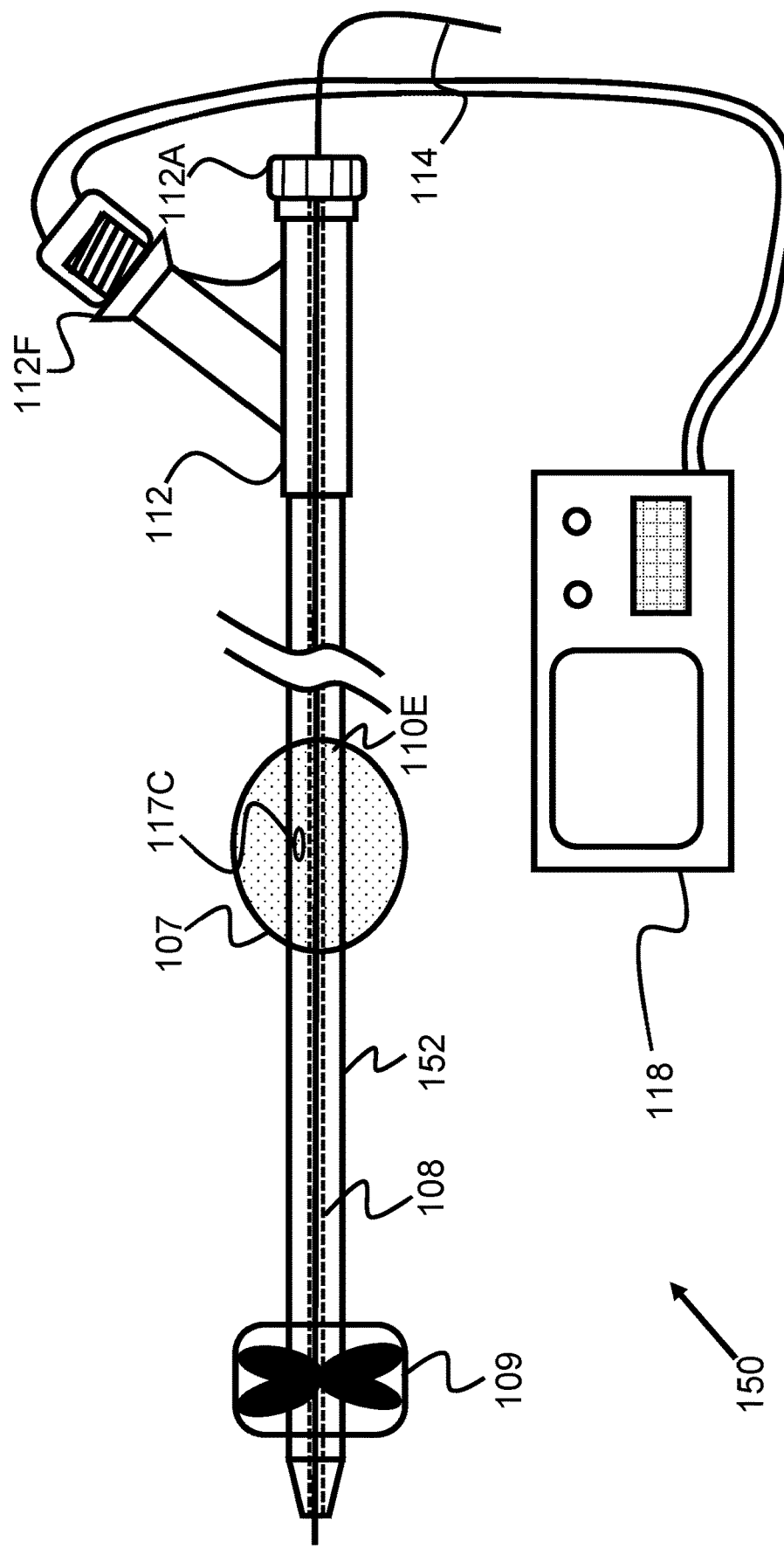
FIG. 16 illustrates a fifth embodiment of the renal perfusion enhancement system using a downstream pump, an upstream balloon, a catheter and a guide wire.

FIG. 16 illustrates another embodiment of a renal perfusion enhancement device 150 where the downstream cycling balloon at the distal end of the catheter 152 is replaced with a downstream impeller pump 109. This type of downstream pump 109 is described in U.S. Pat. No. 9,162,017 to Evans and WIPO Application 2015177793 A2 to Schwammenthal, which are incorporated herein by reference. In one embodiment, the impeller pump 109 of the present invention comprises a bladed rotor, as shown in FIGS. 16-21. When the bladed rotor is placed inside a blood vessel (such as vena cava 12) and rotated, the bladed rotor functions as an impeller by modifying the flow of blood through the blood vessel, and/or by generating a pressure difference between the upstream and the downstream side in the vena cava.

The device 150 of FIG. 16 comprises a single catheter 152 having an inflation lumen 110E and a central lumen 108 disposed within the inflation lumen 110E creating a passageway for a guidewire 114. The guidewire 114 is inserted in the central lumen 108 of the catheter 152 through a connector 112A (e.g., a Touhy-Borst connector) connected to the catheter hub 112 at the proximal end of the catheter 152. A downstream impeller pump 109 is positioned at the distal portion of the catheter 152 and an upstream occlusive balloon 107 is positioned at a proximal portion of the catheter 152. Inflation and deflation of the upstream occlusive balloon 107 is accomplished through inflation aperture 117C placed inside the inflation lumen 110E in the upstream occlusive balloon 107. The inflation lumen 110E of the catheter 152 is connected to a pump system 118 through a connector hub opening 112F. The pump system 118 controls the operation of a pump to inflate and deflate the upstream occlusive balloon 107 of the catheter 152.

In some alternate embodiments, only the downstream impeller pump 109 is positioned at the distal portion of the catheter 152 and the upstream occlusive balloon 107 is absent at the proximal portion of the catheter 152. In some embodiments, the downstream impeller pump 109 is disposed on the catheter 152 such that, when placed in a patient, the downstream impeller pump 109 is either inside renal veins or inside an inferior vena cava and next to the renal veins of the patient.

Figure 17:
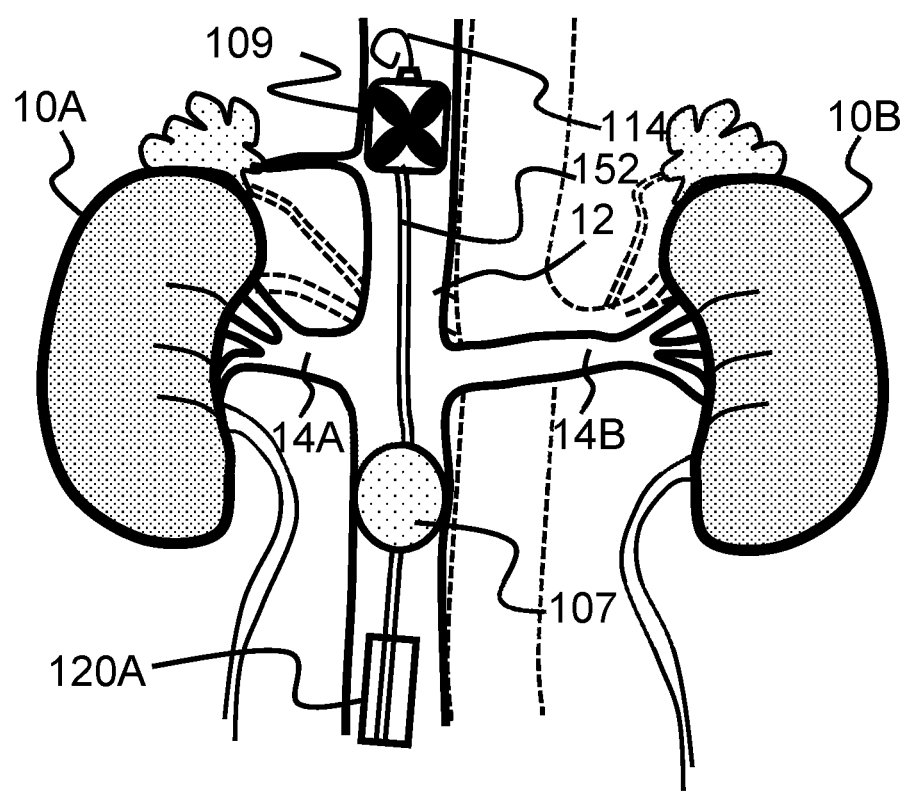
FIG. 17 illustrates the positions of the downstream pump, balloon, catheter and guide wire inside the inferior vena cava.

FIG. 17 illustrates that once the catheter 152 is positioned at the desired location inside the inferior vena cava 12 and next to the right renal vein 14A and left renal vein 14B, the upstream occlusive balloon 107 is inflated first by the controlled operation of the pump system 118 through the inflation aperture 117C. Next, the downstream impeller pump 109 is activated to start pumping fluid out of the kidneys. This pump activation creates a low pressure region within the patient's vena cava 12, adjacent to the junctions of the vena cava with the patient's renal veins 14A and 14B, and the impeller pump 109 pumps blood through the vena cava 12 in the downstream direction, away from the junctions. In the final step, the upstream occlusive balloon 107 is deflated and the whole process is repeated several times to drain excess fluid from kidneys 10A and 10B of the patient.

Figure 18:
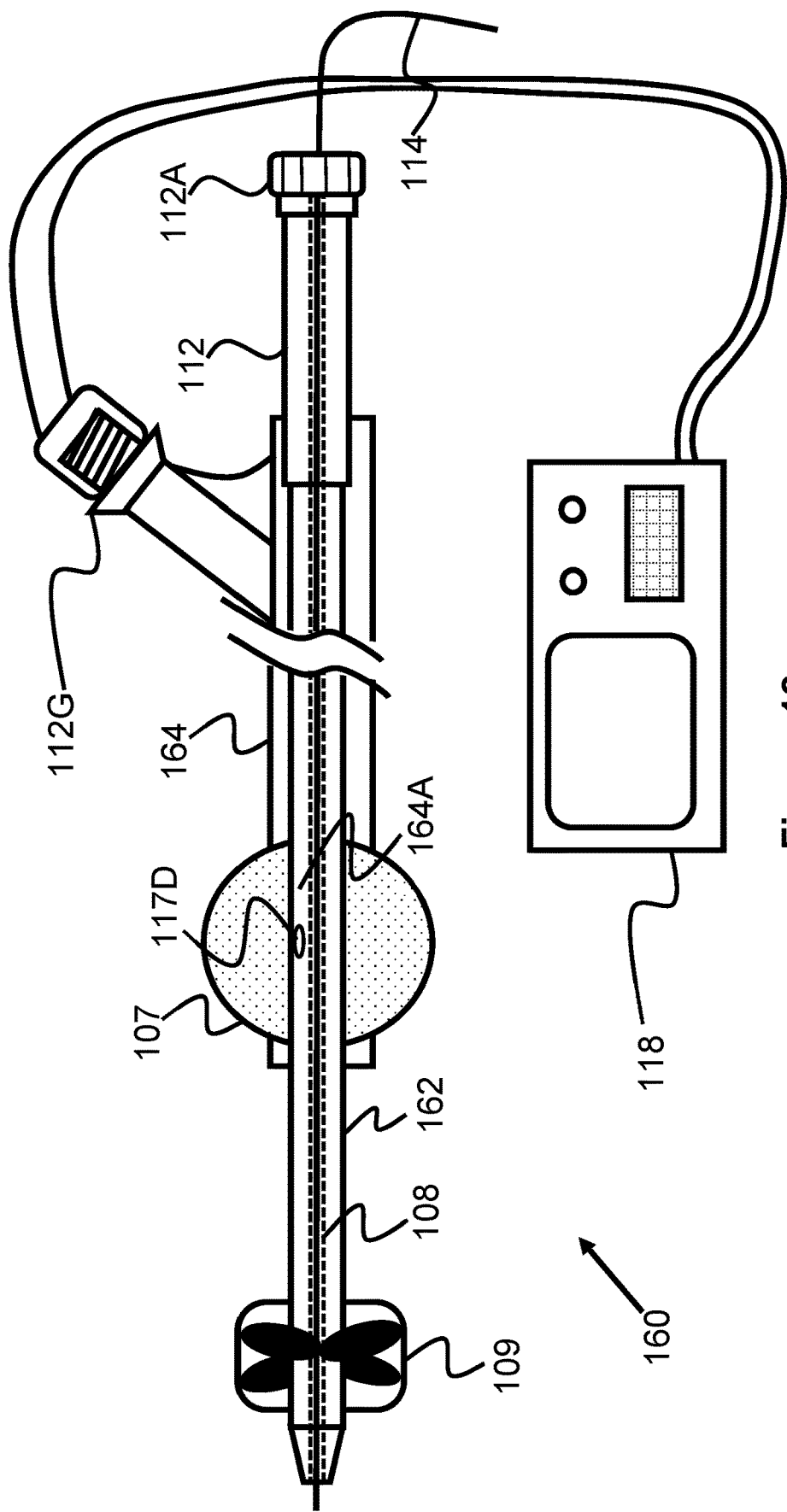
FIG. 18 illustrates a sixth embodiment of the renal perfusion enhancement system using a downstream pump, an upstream balloon, catheters and a guide wire, where the downstream pump and the upstream balloon are placed on different catheters.

FIG. 18 illustrates another embodiment of the renal perfusion enhancement device 160 which comprises a first catheter 162 having a central lumen 108 disposed within creating a passageway for a guidewire 114. The guidewire 114 is inserted in the central lumen 108 of the catheter 162 through an opening 112A connected to the catheter hub 112 at the proximal end of the catheter 162. A downstream impeller pump 109 is positioned at the distal portion of the catheter 162. The device 160 further comprises a second catheter 164 having an inflation lumen 164A and an inflation aperture 117D placed within the catheter 164. An upstream occlusive balloon 107 is positioned at a distal end of the catheter 164. Inflation and deflation of the upstream occlusive balloon 107 is accomplished through the inflation aperture 117D placed in the inflation lumen 110F inside the occlusive balloon 107. The inflation lumen 164A of the catheter 164 is connected to the pump system 118 through a connector hub opening 112G. The pump system 118 controls the operation of a pump to inflate and deflate the upstream occlusive balloon 107 positioned at the distal end of the catheter 164.

Figure 19:
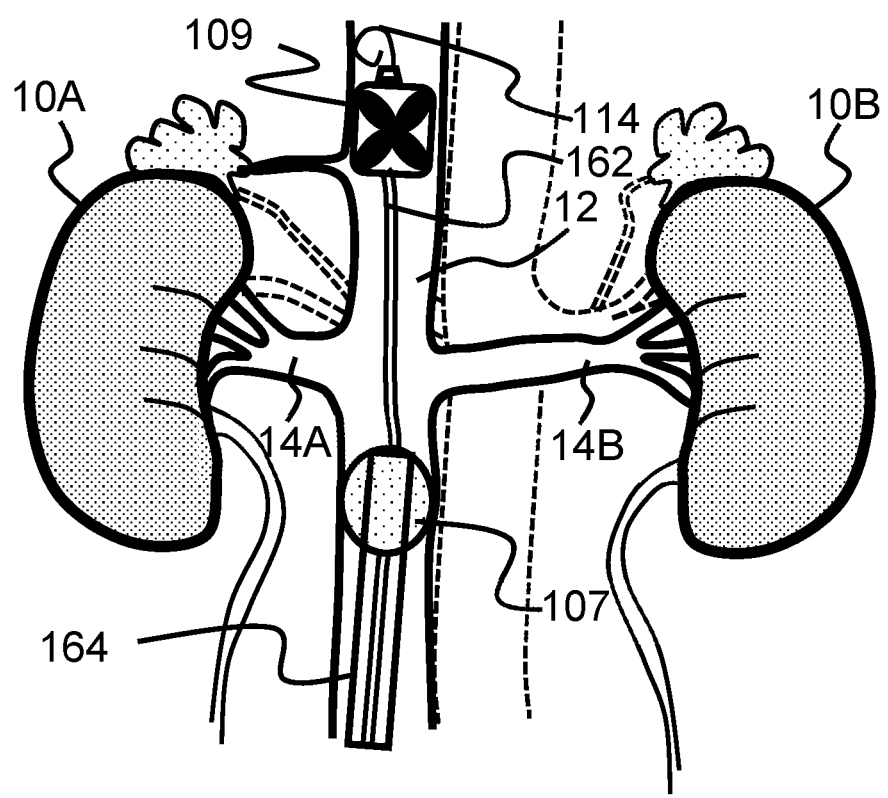
FIG. 19 illustrates the positions of the downstream pump, upstream balloon, catheters and guide wire inside the inferior vena cava.

FIG. 19 illustrates that once the catheter 162 with the downstream impeller pump 109 and the catheter 164 with the deflated upstream occlusive balloon 107 are positioned at the desired location inside the inferior vena cava 12, the upstream occlusive balloon 107 is inflated first by the controlled operation of the pump system 118 through the inflation aperture 117D. Next, the downstream impeller pump 109 is activated to start pumping fluid out of the kidneys 10A and 10B. This pump activation creates a low pressure region within the patient's vena cava 12, adjacent to the junctions of the vena cava with the patient's renal veins 14A and 14B, and the impeller pump 109 pumps blood through the vena cava in the downstream direction, away from the junctions. In the final step, the upstream occlusive balloon 107 is deflated and the whole process is repeated multiples times to drain excess fluid from kidneys 10A and 10B of the patient, preferably to achieve a target urine output amount (e.g., enough times to achieve a target urine output of 1 or more L/day).

Figure 20:
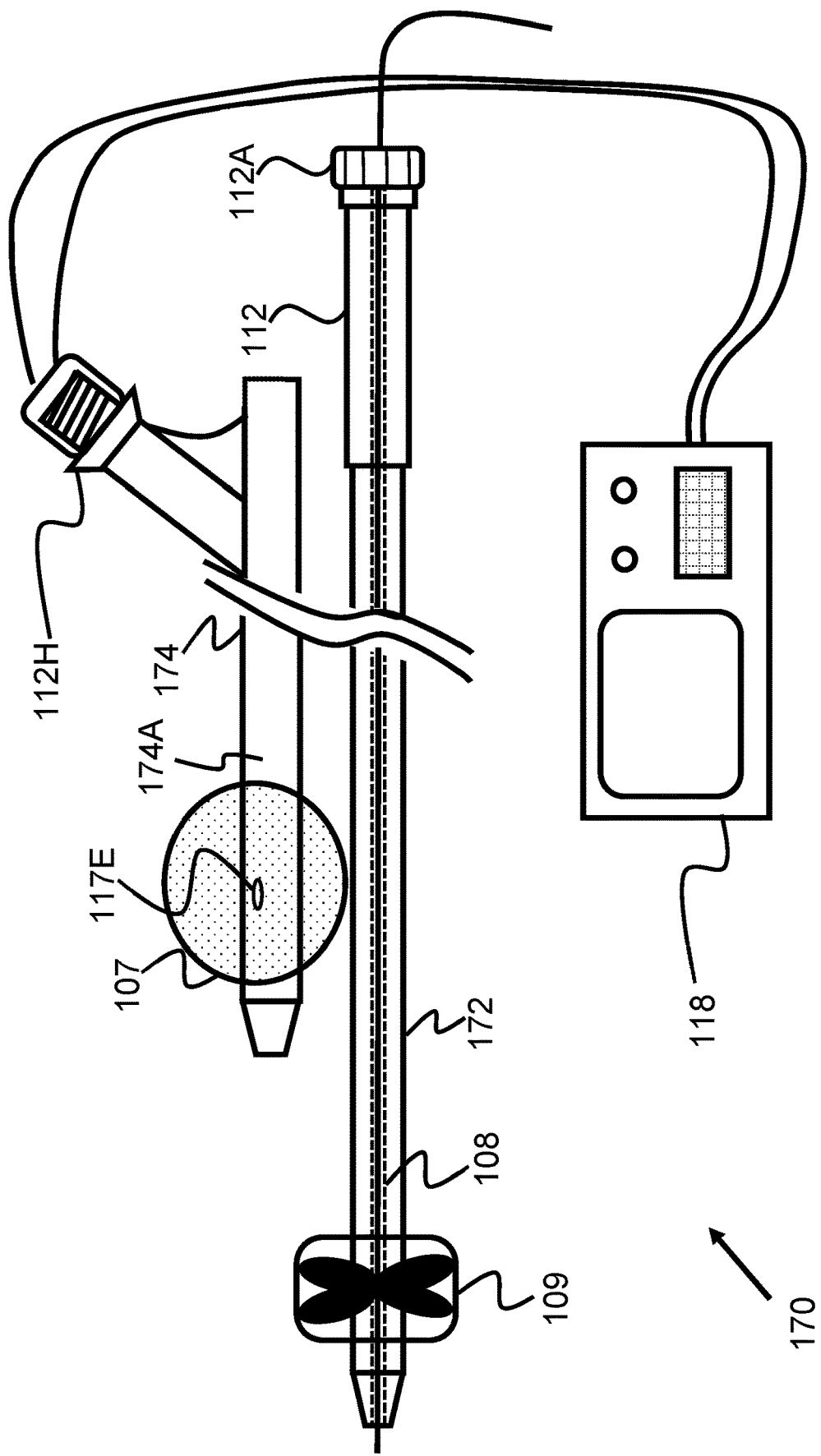
FIG. 20 illustrates a seventh embodiment of the renal perfusion enhancement system using an upstream balloon on a separate catheter and delivered through a one access sheath and a downstream pump on another catheter.

FIG. 20 illustrates an eighth embodiment of the renal perfusion enhancement device 170 which comprises a first catheter 172 having a central lumen 108 disposed within which creates a passageway for a guidewire 114. The guidewire 114 is inserted in the central lumen 108 of the catheter 172 through an opening 112A connected to the catheter hub 112 at the proximal end of the catheter 172. A downstream impeller pump 109 is positioned at the distal portion of the catheter 172. The device 170 further comprises a second catheter 174 having an inflation lumen 174A and inflation aperture 117E. The catheter 174 is delivered through an access sheath (not shown in the drawings) into the vena cava of the patient. An upstream occlusive balloon 107 is positioned at a distal end of the catheter 174. Inflation and deflation of the upstream occlusive balloon 107 is accomplished through the inflation aperture 117E placed in the inflation lumen 174A inside the occlusive balloon 107. The inflation lumen 174A of the catheter 174 is connected to the pump system 118 through a connector hub opening 112H. The pump system 118 controls the operation of the pump to inflate and deflate the upstream occlusive balloon 107 of the catheter 174.

Figure 21:
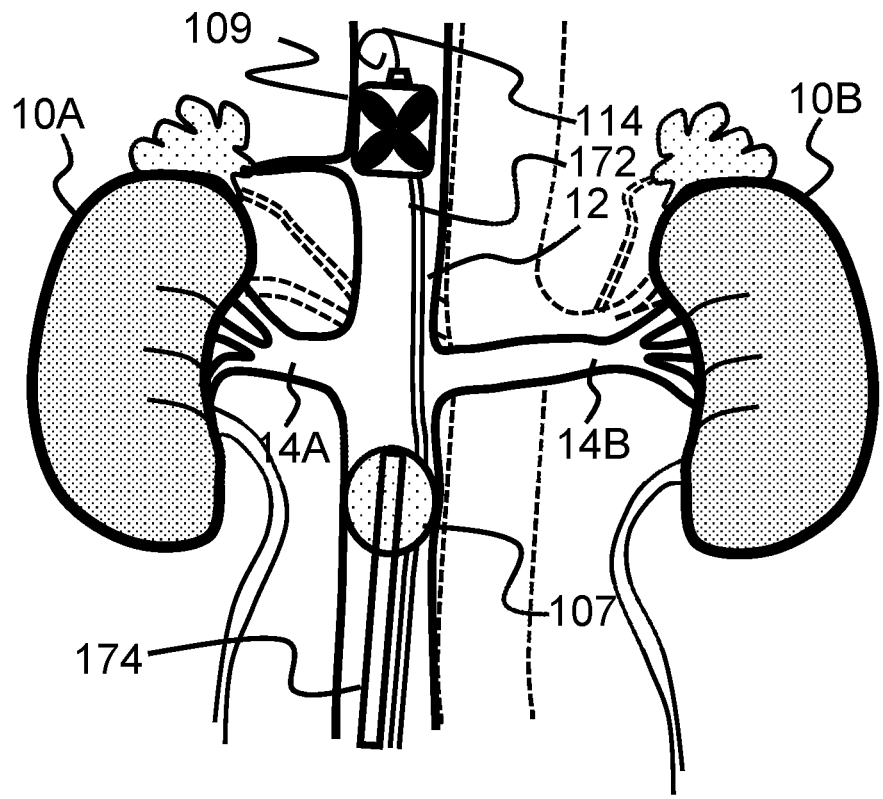
FIG. 21 illustrates the positions of the downstream pump, upstream balloon, catheters and guide wire inside the inferior vena cava.

FIG. 21 illustrates that once the catheter 172 with the downstream impeller pump 109 and the catheter 174 with the deflated upstream occlusive balloon 107 are positioned at the desired location inside the inferior vena cava 12, the upstream occlusive balloon 107 is inflated first by the controlled operation of the pump system 118 through the inflation aperture 117E. Next, the downstream impeller pump 109 is activated to start pumping fluid out of the kidneys 10A and 10B. This impeller pump 109 activation creates a low pressure region within the patient's vena cava 12, adjacent to the junctions of the vena cava with the patient's renal veins 14A and 14B, and the impeller pump 109 pumps blood through the vena cava 12 in the downstream direction, away from the junctions. In a final step, the upstream occlusive balloon 107 is deflated and the whole process is repeated three times to drain excess fluid from kidneys 10A and 10B of the patient.

Figure 22:
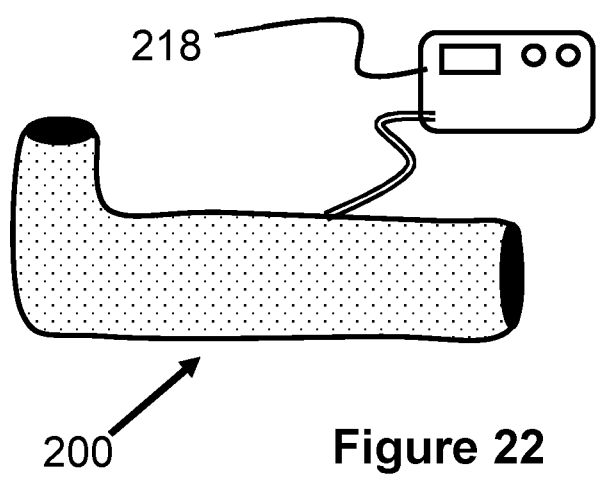
FIG. 22 illustrates an external pumping device for lymphatic drainage.

FIG. 22 illustrates an automatic pneumatic external sleeve 200 that can be used to augment lymphatic flow and decrease congestion in acute decompensated heart failure in patients. Specifically, the pneumatic external sleeve 200 can be used in combination with any of the previously described techniques in this specification (i.e., before, during, and/or after a procedure). The pneumatic external sleeve 200 is connected to a pump processor 218 and which increases the air pressure within the sleeve 200. Preferably, the sleeve is placed over the patient's legs which tends to be a location where excess fluid gets collected. The pressure from the sleeve 200 may help drive fluid upwards, which may increase the effectiveness of the prior described embodiments.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for enhancing renal perfusion of a patient comprising:
   placing a device with a proximal upstream occlusive balloon and a distal downstream cycling balloon inside an inferior vena cava of the patient;
   inflating the proximal upstream occlusive balloon;
   inflating the distal downstream cycling balloon in a manner to prevent a rapid increase in pressure inside renal veins; and
   deflating the distal downstream cycling balloon in a manner so as to create a low-pressure zone for directing blood from the kidneys and into the inferior vena cava in a downstream direction.

2. The method of claim 1, wherein placing the distal downstream cycling balloon comprises placing the distal downstream cycling balloon within the inferior vena cava downstream of a junction of the inferior vena cava and said renal veins of the patient.

3. The method of claim 1, wherein the device includes a single catheter, and wherein the placing of the upstream occlusive balloon and the downstream cycling balloon into the inferior vena cava is performed with the single catheter.

4. The method of claim 1, wherein the device includes first and second catheters, and wherein the placing of the upstream occlusive balloon and the downstream cycling balloon into the inferior vena cava is performed with the first and the second catheters, respectively.

5. The method of claim 4, wherein the placing of the upstream occlusive balloon into the inferior vena cava comprises inserting the second catheter having said upstream occlusive balloon positioned at a distal end of the second catheter.

6. The method of claim 5, wherein the placing of the upstream occlusive balloon into the inferior vena cava further comprises delivering the second catheter through an access sheath.

7. The method of claim 1 further comprises placing only the distal downstream cycling balloon either inside the renal veins or inside the inferior vena cava and next to the renal veins of the patient.

8. The method of claim 1 further comprises performing the inflating and deflating of the proximal upstream occlusive balloon multiple times.

9. An apparatus for renal perfusion enhancement comprising:
   a delivery device;
   an upstream occlusive balloon disposed on a proximal end of the delivery device;
   a downstream cycling balloon disposed on a distal end of the delivery device;
   a control unit configured to control inflation and deflation of the upstream occlusive balloon and the downstream cycling balloon;
   wherein, a low pressure zone is configured to be created for directing blood through the inferior vena cava in a downstream direction when the downstream cycling balloon is configured to be deflated while the upstream occlusive balloon is configured to remain inflated.

10. The apparatus according to claim 9, wherein the control unit is further configured to cycle the inflation and deflation of said downstream cycling balloon.

11. The apparatus according to claim 9, wherein the delivery device is a single catheter, and wherein the upstream occlusive balloon and the downstream cycling balloon are placed on said single catheter.

12. The apparatus according to claim 9, wherein the delivery device includes first and second catheters, and wherein the upstream occlusive balloon and the downstream cycling balloon are placed on said first and said second catheters.

13. The apparatus according to claim 12, wherein the upstream occlusive balloon is disposed at a distal end of said second catheter.

14. The apparatus according to claim 13, wherein an access sheath of said apparatus is used to insert the second catheter inside said inferior vena cava of the patient.

15. The apparatus according to claim 9, wherein only the downstream cycling balloon is disposed on a distal end of the catheter.

16. The apparatus according to claim 15, wherein the downstream cycling balloon is disposed on said catheter such that, when placed in a patient, said downstream cycling balloon is either inside renal veins or inside an inferior vena cava and next to the renal veins of the patient.

17. The apparatus according to claim 9, wherein the downstream cycling balloon is configured for progressive inflation in diameter along a length of the downstream cycling balloon.

18. The apparatus according to claim 17, wherein the progressive inflation of the downstream cycling balloon includes either various diameters of inflation apertures of the catheter or areas of different elasticity or hardness along the length of the downstream cycling balloon.

19. The method of claim 1, wherein inflating the distal downstream cycling balloon in a manner to prevent said rapid increase in pressure inside said renal veins comprises inflating the distal downstream cycling balloon slowly and gradually over a period of about 10 seconds to 20 seconds.

20. The method of claim 1, wherein deflating the distal downstream cycling balloon in a manner so as to create said low-pressure zone comprises deflating the distal downstream cycling balloon rapidly over a period of about 1 second to 4 seconds.

* * * * *